(12) United States Patent
Yatcilla et al.

(10) Patent No.: US 7,226,626 B2
(45) Date of Patent: *Jun. 5, 2007

(54) FOOD PRODUCTS AND DIETARY SUPPLEMENTS CONTAINING PHENOLATED PROTEINS AND PROCESS FOR PREPARING THE SAME

(75) Inventors: Michael T. Yatcilla, Irvine, CA (US); Gilbert Gluck, Irvine, CA (US)

(73) Assignee: Cyvex, Technologies, Inc., Irvine, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 10/834,333

(22) Filed: Apr. 28, 2004

(65) Prior Publication Data

US 2004/0202733 A1    Oct. 14, 2004

Related U.S. Application Data

(60) Continuation of application No. 09/904,713, filed on Jul. 12, 2001, now Pat. No. 6,753,312, and a division of application No. 09/904,713, filed on Jul. 12, 2001, now Pat. No. 6,753,312.

(51) Int. Cl.
*A61K 35/78* (2006.01)
*A61K 38/16* (2006.01)

(52) U.S. Cl. .................. 424/756; 424/757; 424/776; 514/2; 514/12

(58) Field of Classification Search .............. None
See application file for complete search history.

(56) References Cited

U.S. PATENT DOCUMENTS 4,435,319 A    3/1984 Pearce
5,762,936 A *  6/1998 Ronzio et al. ............ 424/757

OTHER PUBLICATIONS

Xu et al. "Interactions between canola proteins and phenolic compounds in aqueous media" 2000, Food Research International, vol. 33, issue 9, pp. 725-731, abstract.*
Parr et al "Phenols in plant and man.the potential for possible nutrional enhancement of the diet by modifying the phenols content or profile" J. Sci. Food Agric. 80:985-1012 (2000).*
Vinson, et al., Phenol Antioxidant Quantity and Quality in Foods: Vegetables, J. Agric. Food Chem., 1998, 3630-3634, vol. 46.
Parr, et al., Phenols in the Plant and Man. The Potential for Possible Nutritional Enhancement of the Diet by Modifying the Phenols Content or Profile, J. Sci. Food Agric., 2000, 985-1012, vol. 80.
Cao, et al., Automated Assay of Oxygen Radical Absorbance Capacity with the COBAS FARA II, Clinical Chemistry, 1995, 1738-1744, vol. 41/12.
Food Phenolics, Chapter 6, 1995, 171-179.
Kayashita, et al., Hypocholesterolemic Effect of Buckwheat Protein Extract in Rats Fed Cholesterol Enriched Diets, Nutrition Research, 1995, 691-698, vol. 15.
Kayashita, et al., Consumption of Buckwheat Protein Lowers Plasma Cholesterol and Raises Fecal Neutral Sterols in Cholesterol-Fed Rats Because of its Low Digestibility, Journal of Nutrition, 1997, 1395-1400, vol. 127.
Kayashita, et al., Buckwheat Protein Extract Suppression of the Growh Depression in Rats Induced Feeding Amaranth (Food Red. No. 2), Biosci. Biotechnol. Biochem., 1996, 1530-1531, vol. 60.
Kayashita, et al., Current Advances in Buckwheat Research, 1995, 935.
Kayashita, et al., Muscle Hypertrophy in Rats Fed on Buckwheat Protein Extract, BioSci. Biotechnol. Biochem., 1999, 1837-1839, vol. 63.
Kayashita, et al., Consumption of a Buckwheat Protein Extract Retards 7,12-Dimethylbenz[α] anthracene-Induced Mammary Carcinogenesis in Rats, BioSci. Biotechnol. Biochem, 1999, 1837-1839, vol. 63.
Loomis, et al., Plant Phenolic Compounds and the Isolation of Plant Enzymes, Phytochemistry, 1966, 423, vol. 5.
Lucas, et al., Sunflower Seed Protein, New Protein Foods, 1985, 393-433, vol. 5.
Prior, et al., Variability in Dietary Antioxidant Related Natural Product Supplements; the Need for Methods of Standardization, J. Amer. Nutraceutical Assoc., 1999, 46-56, vol. 2.
Rao, et al., Bioabsorption In Vivo Antioxidant Properties of Grape Extract Biovin: A Human Intervention Study, J. Medicinal Food, 2000, 15-22, vol. 3, No. 1.
Sodini, et al., Acidic Butanol Removal of Color-Forming Phenols from Sunflower Meal, J. Agric. Food Chem., 1977, 822-825, vol. 25.
Kayashita et al., BioSci. Biotechnol. Biochem., 63, 1242, 1999.

* cited by examiner

*Primary Examiner*—Cecilia Tsang
*Assistant Examiner*—Roy Teller
(74) *Attorney, Agent, or Firm*—Gabor L. Szekeres

(57) ABSTRACT

Novel food, dietary supplement and nutraceutical products containing phenol/protein complexes derived from vegetable sources have high antioxidant activity and very high levels of protein. The products provide novel means for administering high levels of plant antioxidants to human and mammals in the form of a protein concentrate. Due to their high antioxidant capacity these novel products are useful as aids in the prevention and treatment of many diseases.

14 Claims, No Drawings

FOOD PRODUCTS AND DIETARY SUPPLEMENTS CONTAINING PHENOLATED PROTEINS AND PROCESS FOR PREPARING THE SAME

CROSS-REFERENCE TO RELATED APPLICATION

The present application is a continuation/divisional of application Ser. No. 09/904,713 filed on Jul. 12, 2001, to be issued as U.S. Pat. No. 6,753,312

FIELD OF THE INVENTION

The present invention is in the field of dietary supplements and foods. More particularly, the present invention relates to dietary supplements and food products containing phenolated protein substances having anti-oxidant properties, and to the process of manufacturing such dietary supplements and food products from vegetable sources for oral consumption by humans.

BRIEF DESCRIPTION OF BACKGROUND ART

It has been known for a long time that many plant materials contain phenols or phenolic compounds. The term phenols, phenolic compounds or plant phenolics in the context of plant materials and in the context of the present application for patent refer to a multitude of naturally occurring substances which have one or more phenolic hydroxyl groups. As is known, a phenolic hydroxyl group is a hydroxyl group (OH) attached to a carbocyclic aromatic ring. Phenol (hydroxybenzene) is the simplest example of a phenolic compound, but the naturally occurring phenols or phenolic compounds tend to be of more complex structure, and include polyphenols having complex substitution patterns and compounds having condensed rings. Phenolics isolated from plants including seeds and fruits of plants include gallic acid, flavan-3-ols, flavonols, phloridzin, cinnamates, hydroxymethyl furfural and anthocyanins.

Phenolics compounds contained in plant materials, particularly in plant materials from which proteins are isolated for human or animal consumption, have long been considered undesirable. This is primarily because phenolics tend to bind strongly to proteins (by hydrogen bonds) and also by covalent bonds, and tend to provide undesired color to the plant protein isolates. Whereas the present applicant does not wish to be bound by theory, it is noted that the process by which phenolic compounds are bound to proteins is generally understood to involve a step of oxidation that occurs while the plant isolate is in aqueous suspension or solution, and is exposed to atmospheric oxygen, or to oxygen dissolved in water, followed by a 1,4 addition (Michael addition) of a sulfhydryl (SH) or amino (NH) function of the protein to the resulting quinone. This series of reactions is illustrated below in a simplified form. The reaction below is simplified, because the plant phenolic compound is not simple phenol or hydroquinonone as illustrated below, but a more complex phenolic compound of the nature described above. The group R in the simplified scheme represents the rest of the plant protein molecule, just like the simple phenol or hydroquinone in the simplified scheme represents the more complex phenolic compound naturally occurring in the plant.

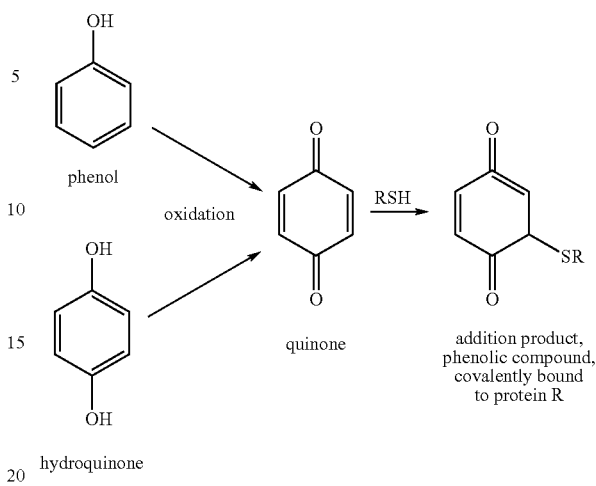

A detailed description and review of the chemistry of the attachment of plant phenolics to plant proteins by hydrogen bonding and through oxidation to quinones followed by 1,4 (Michael) addition, can be found in the publication by Loomis et al., "Plant phenolic compounds and the isolation of plant enzymes" Phytochemistiy, 5,423, (1966).

Because the plant phenolics are generally considered in the prior art to be undesirable contaminants of proteins which are isolated from the plant, the prior art has strived to isolate the proteins flee of the phenolics, and to discard the undesirable phenolics while keeping the desired protein material. Thus, processes for removing the phenolics from plant proteins, and to isolate proteins as free of phenolic contaminants as possible, are described in several publications and patents, such as:

Lusas "Sunflower Seed Protein", New Protein Foods, 5, 393-433, (1985);

Sodini et al. J. Agric. Food Chem., 25, 822-825, (1977), and

Pearce U.S. Pat. No. 4,435,319.

Perhaps because of the difficulty or expense of removing "undesirable" phenolics from phenolics-rich plant flours, the phenol-rich flours are typically considered to be of poor quality for human or animal consumption and are hence abundant and inexpensive. These typically are by-products of oil extraction (e.g., flax meal) or represent a by-product of a specialized milling fraction (e.g., buckwheat).

In addition to being considered undesirable as a colorant, plant phenolics were also suggested to have anti-nutritive value (Food Phenolics, Chapter 6, p. 171-9, 1995).

On the other hand, it has been relatively recently recognized in the prior art that oral consumption of antioxidants increases serum antioxidant levels (see Rao et al., J. Medicinal Food, Mar. 15, 2000) and that orally consumed anti-oxidants have beneficial value to human (and other mammalian) health. More specifically, the health benefits or potential benefits shown by epidemiological studies and generally attributed to consumption of anti-oxidant rich food or food supplements include or relate to prevention of various cancers, decrease in the incidence of cardiovascular disease, and decrease in the incidence of stroke. Recognizing the importance of anti-oxidants in foods or food supplements, the prior art has actually developed an assay for determining the amount of anti-oxidants contained in a food product. The assay termed the Oxygen Radical Absorbance Capacity Assay (ORAC) is described by Cao et al., in Clinical Chemistry, 41, 1738, 1995. This assay allows one to quickly compare the total antioxidant capacity of various food servings (Prior et al. J. Amer. Nutraceutical Assoc., 2, 46, (1999)).

As an exception to the prior art generally making great efforts to remove undesirable phenolics from isolated plant proteins, buckwheat protein from which phenolics have not been removed has been reportedly fed to experimental rats, as is described in a series of publications:

Kayashita et al., Nutrition Research, 15, 691-8, 1995;
Kayashita et al., J. Nutrition 127, 1395, 1997;
Kayashita el al., Biosci. Biotechnol. Biochem., 60, 1530, 1996;
Kayashita et al., Current Advances in Buckwheat Research, 935, 1995;
Kayashita et al., BioSci. Biotechnol. Biochem., 63, 1242, 1999, and
Kayashita et al., BioSci. Biotechnol. Biochem., 63, 1837, 1999.

In these publications about buckwheat protein, the authors suggest that whatever health effects were observed in the experimental rats they were entirely due to the protein composition of the buckwheat versus soy protein or casein. The authors discuss in detail the amino acid profiles of buckwheat protein and find several features of buckwheat protein that suggest health benefits. Indeed, buckwheat has been shown in the prior art to have great health benefits independent of its protein or phenol content. Hence, any phenolic compounds which may have been present in the buckwheat protein of these experiments would have been considered impurities, and thus feeding of protein-phenol complexes to animals is not suggested by these publications of Kayashita et al.

SUMMARY OF THE INVENTION

It is an object of the present invention to provide a food supplement, food product or nutraceutical which is rich in vegetable protein bound plant phenolics having anti-oxidant properties.

It is another object of the present invention to provide a food supplement, food product or nutraceutical which is rich in vegetable protein bound plant phenolics having anti-oxidant properties and which utilizes readily available relatively inexpensive plant sources for the manufacture of such products.

It is still another object of the present invention to provide a process for the manufacturing of food supplements, food products or nutraceuticals which are rich in vegetable protein bound plant phenolics having anti-oxidant properties.

These and other objects and advantages are attained in accordance with one aspect of the invention by isolating protein material from vegetable sources of the type which is known to contain relatively high concentration of plant phenolics, such as buckwheat, sunflower seeds, soy beans, hops, mustard seeds, cottonseeds, peanuts, safflower seeds, rapeseed, flax seeds, by dissolving or suspending flour from said vegetable source in water, adding base to make the aqueous solution alkaline in a pH range of approximately 8 to 13, allowing oxidation of phenolic materials to occur by exposure to air or to oxygen dissolved in the water, acidifying the solution to a pH in the range of 2 to 7 by addition of acid, isolating the precipitated solids containing plant phenolics covalently bound to proteins, and incorporating said isolated plant phenolics covalently bound to proteins in foods, food supplements and in nutraceutical products.

In accordance with another aspect of the present invention exogenous phenolic products, such as phenolic acids (caffeic acid, gallic acid), catechins (epicatechin, catechin, gallocatechin gallate, epigallocatechin gallate), flavones (quercetin, myricetin, kaempherol), anthocyanidins (cyanidin, delphinidin, malvidin), or isoflavones (diadzein, genistein) are added to the vegetable flour dissolved or suspended in water, before it is rendered alkaline or while it is alkaline, so that the exogenous phenolics also bind covalently to the vegetable protein. Thereafter, the phenolics bound to the protein is isolated and utilized in the above-described manner. The isolated vegetable protein bound phenolics containing phenolics from the natural source and the added phenolics as well, are also incorporated in foods, food supplements and nutraceutical products.

The foods, food supplements and nutraceutical products of the invention have high antioxidant capacity as measured by the aforesaid Oxygen Radical Absorbance Capacity Assay (ORAC) test. The products of the invention having vegetable protein bound phenolics include, drinks such as shakes, bars, capsules, tablets, soft-gel capsules and other conventional forms in which foods, food and dietary supplements and nutraceuticals are provided for human consumption.

DETAILED DESCRIPTION OF THE INVENTION

Vegetable protein bound phenolics can be obtained in accordance with the present invention from all such vegetable sources which usually serve as sources for vegetable proteins, for example buckwheat, sunflower seeds, soy beans, hops, mustard seeds, cottonseeds, peanuts, safflower seeds, rapeseed and flax seeds. The flour from these vegetable sources usually contains naturally occurring phenolics. As noted in the introductory section, the prior art has usually strived to separate the phenolics from the vegetable protein and discard it. In accordance with the present invention these naturally occurring phenolics are allowed to bind covalently to the protein.

Flour of the vegetable, such as of the above-noted buckwheat, sunflower seeds, soy beans, and others is first obtained in the manner well established in the art, which need not be described here. The vegetable flour, for example buckwheat flower, typically contains approximately 10 percent (by weight) of protein and approximately 1 percent (by weight) of phenolics. (All percentages in the present description are on a weight by weight basis, unless noted otherwise.)

In accordance with the process of the invention the vegetable flour is dissolved or suspended in a large excess of water, and while the solution or suspension is agitated alkali, such as sodium hydroxide or other nutritionally acceptable alkaline substance, is added until the pH of the solution/suspension is adjusted within the range of 8 to 13. A preferred pH range is 9.5 to 11.0. The alkaline solution/suspension is continuously agitated, preferably at an elevated temperature, such as in the range of 30 to 70° C., for sufficient time for the dissolved phenolics to undergo some oxidation to quinones and subsequent covalent attachment to the dissolved vegetable protein, probably by the chemical reactions described in the introductory section of this application for patent. In this connection again it is noted that whereas the above-described 1,4 (Michael) addition reaction is believed to be the predominant reaction by which the oxidized or partially oxidized phenolic compounds attach to the vegetable proteins under alkaline conditions, the present applicant does not wish to be bound by theory. Those skilled in the art will readily understand that the time required or utilized for the phenolics to undergo the above-described oxidation to quinones and covalent attachment depends on several factors, such as the temperature, the speed of agitation and the precise nature of the phenolics and of the protein. However, agitation under alkaline condition at an elevated temperature for a period of approximately 15 minutes to 2 hours is usually sufficient, a more preferred range of time is between 30 minutes to 1 hour.

In the next step of the process of the invention solids are removed from the alkaline solution/suspension by centrifugation or filtration. Generally speaking the removed solid materials comprise wet plant hulls, fibers and other insolubles and have no further significance or value from the stand-point of the present invention, and usually are discarded.

In the following step of the process, a nutritionally acceptable form of acid, such as hydrochloric acid is added to the liquid obtained previously by filtration or centrifugation until the pH is brought down into a range of approximately 2 to 7, preferably into a range of 3.5 to 5.0. The liquid is preferably agitated while the acid is added, and preferably the mixture is allowed to warm spontaneously to, or if necessary is heated to an elevated temperature in the range of 30 to 70° C. A presently preferred temperature both for the step of adjusting the pH to alkaline in the first step, and for acidifying the filtered solution in the present step is 55° C. Nevertheless, those skilled in the art will understand that these process steps can be performed at ambient temperature as well. The acidified solution is allowed to agitate for a period of time, preferably in the range of 15 minutes to 2 hours, more preferably for 30 minutes to 1 hour, although the time is not critical. As a result of the acidification, vegetable protein and the vegetable protein bound phenolics precipitate out of the acidic solution, and are collected by filtration of centrifugation. After these solids are collected, the remaining liquid (supernatant) has no significance or value from the view point of the present invention, and can be utilized for other applications, or is discarded.

The collected solid material comprises vegetable protein bound phenolics and may also comprise vegetable protein molecules which have no phenolic moiety attached. Nevertheless, for the purpose of the present description the collected solid material is referred to as vegetable protein bound phenolics, with the understanding that, although this material is "rich" in phenolics, the bulk of its mass is composed of protein molecules, with the phenolics being randomly attached to the protein.

The collected solid is wet, and can subsequently be dried in processes and apparatus normally used in the food processing and related industry for this purpose. Typically, the solids are dried in an atomizing spray drier, to yield a dry product rich in bound phenolics. The dry product obtained in this manner typically has an antioxidant capacity of 50 to 200 micromoles of trolox equivalent per mg. By comparison, soy protein isolate, containing 90% protein, 4% moisture, 4% ash, 1% fat, 1% carbohydrate, typically has an antioxidant capacity of 18 micromoles trolox equivalents per milligram.

This product, the vegetable protein bound phenolics, is then admixed with usual excipients known in the art to make tablets, capsules, soft-gel capsules or like delivery vehicles, in which the content of vegetable protein bound phenolics obtained above comprise approximately 25 to 95 weight percent of the tablet, capsule, soft-gel capsule or like delivery vehicle, and which typically have an antioxidant capacity of 10 to approximately 200 micromoles of trolox equivalent per mg of total material contained in the tablet, capsule, sof-gel capsule or like delivery vehicle. Stated in another way, typically each unit dose (tablet, capsule, soft gel capsule or the like) of the dietary supplement has an antioxidant capacity of 2500 to 200,000 micromoles of trolox equivalent per unit dose, and preferably approximately 20,000 to 100,000 micromoles of trolox equivalent per unit dose.

It should be understood in this connection that the excipient may or may not itself have nutritive value (for example it may include sugars and starch), and that the tablets, capsule, soft-gel capsules or like delivery vehicles may contain additional vitamins, minerals or other known nutraceutical products. The term "excipient" as it is used in this description intends to cover all such ingredients which may be included in the tablets, capsules, soft-gel capsules and the like that contain the vegetable protein bound phenolics in accordance with the invention.

Alternatively, the vegetable protein bound phenolics obtained above are incorporated in liquid or solid foods, such as shakes or bars, which typically have an antioxidant capacity of 500 to 20,000 micromoles of trolox equivalent per gram of the shake, bar or other food. The shakes, bars or other food products contain one or more conventional ingredients having nutritional and/or caloric value, such as sugars, syrups, chocolate, cocoa powder, natural or artificial flavors such as chocolate, vanilla or other flavors, lecithin, fats or oils (preferably vegetable oils) proteins from sources other than the vegetable protein bound phenolics of the invention. All the conventional nutritional products having caloric value and the flavor producing and other conventional ingredients are collectively termed "nutritional products" for the purposes of the present description. In addition to containing the vegetable protein bound phenolics and nutritional products, the shakes, bars or other food products of the invention may also contain vitamins, minerals or other known nutraceutical products.

In accordance with another aspect of the present invention, additional phenolic material of the type which itself occurs naturally in many plants is added to the aqueous admixture of the vegetable flour before or while it is kept under alkaline condition. Exogenous phenolic materials which can be added to the vegetable protein in accordance with this aspect of the invention, include phenolic acids (caffeic acid, gallic acid), catechins (epicatechin, catechin, gallocatechin gallate, epigallocatechin gallate), flavones (quercetin, myricetin, kaempherol), anthocyanidins (cyanidin, delphinidin, malvidin), or isoflavones (diadzein, genistein). The structure of quercetin is shown below. Generally speaking, 0.25 to 5 lbs of exogenous phenolic material (such as quercetin or any of the substances noted above, or combination of such phenolic substances) is added to 100 lbs of vegetable flour; the preferred range being 0.5 to 2.0 lbs of exogenous phenolics by 100 lbs of vegetable flour, and a presently most preferred number is 1 lb of quercetin per 100 lbs of vegetable flour.

The remaining steps of the process are then conducted as described above. In this manner, still higher concentrations of vegetable protein bound phenolics are contained in the final dried product, having an antioxidant capacity of 200 to 2000 micromoles of trolox equivalent per mg of the product. This product also, is made into tablets, capsules, soft-gel capsules or other delivery vehicles, or is incorporated into food products, such as shakes and bars. Depending on the amount of excipient used to make the tablets, capsules, soft-gel capsules or like delivery vehicles, these have an antioxidant capacity of 50 to 2000 micromoles of trolox equivalent per mg of total material contained in the tablet, capsule, soft-gel capsule or like delivery vehicle (as above). Or stated in another way, each unit dose (tablet, capsule, soft-gel capsule or the like) has a an antioxidant capacity of 12,500 to 2,000,000 micromoles of trolox equivalent per unit dose and preferably 100,000 to 500,000 micromoles of trolox equivalent per unit dose.

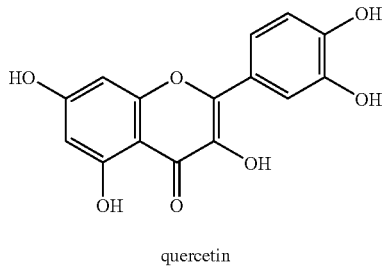

quercetin

Thus, in accordance with the present invention valuable foods, food or dietary supplements or nutraceuticals are obtained from materials which in the prior art were considered of little value. The present invention essentially contradicts the teaching in the prior art which taught that it was necessary to remove phenolic materials from vegetable protein isolates.

SPECIFIC EXAMPLES

Example 1

Buckwheat Phenol/Protein Isolation 93 lbs. of buckwheat (*fagopyrum esculentum* L.) flour were added to 120 gallons of water. pH was adjusted to 10.05 by adding 2910 ml of 30% NaOH. Temperature was held at 55° C. under constant agitation for 30 minutes. The resultant mixture was pumped into a solids-ejecting disc centrifuge with a back pressure of 58 psi and a de-sludging cycle time of 3 minutes. The solids ejected by the centrifuge, consisting mostly of wet plant hulls, fiber and other insolubles, weighing 383 lbs. were discarded. The liquids were pumped through a 20 micron cartridge prefilter into a second tank. pH was adjusted to 4.5 using 30% HCl to precipitate the phenol-protein complex. Temperature was kept at 55° C. for 30 minutes. The resultant mixture was pumped into a solids-ejecting disc centrifuge with a back pressure of 58 psi and a de-sludging cycle time of 4 minutes. The liquids that passed through the centrifuge (568 lbs.), consisting mostly of soluble carbohydrates and phenols not complexed to proteins, were kept for another application. The solids ejected by the centrifuge (136.5 lbs.) consisting of the phenol/protein complex, were collected and fed into an atomizing spray drier of standard design using a Moyno pump at 1 gallon per minute flow rate. The product was sprayed from an atomizer with 4 mm orifices into a 7 foot-high tower. The spray-drier inlet temperature was 410° F. and the outlet temperature was 190° F.

16 lbs. of dried product was obtained from the spray drier. The resultant product consisted of 64.3% protein, 4.0% moisture, 9.0% fat, 2.7% ash, and 20.0% carbohydrate. The product contained 0.4% free phenolic material. The product had an antioxidant capacity of 101 micromoles trolox equivalents per milligram. By comparison, soy protein isolate, containing 90% protein, 4% moisture, 4% ash, 1% fat, 1% carbohydrate, had an antioxidant capacity of 18 micromoles trolox equivalents per milligram.

Example 2

Introduction of Exogenous Phenols to a Buckwheat Phenol/Protein Isolation 100 lbs. of buckwheat (*fagopyrum esculentum* L.) flour and 1 lb. of quercetin were added to 100 gallons of water. pH was adjusted to 11.02 by adding 30% KOH. Temperature was held at 55° C. under constant agitation for 45 minutes. The resultant mixture was pumped into the same solids-ejecting disc centrifuge as described in Example 1. The solids ejected by the centrifuge, consisting mostly of wet plant hulls, fiber and other insolubles, were discarded. The liquids were pumped through a 20 micron cartridge prefilter into a second tank. pH was adjusted to 4.03 using 30% HCl to precipitate the phenol-protein complex. Temperature was kept at 55° C. for 30 minutes. The resultant mixture was pumped into a solids-ejecting disc centrifuge. The liquids that passed through the centrifuge (472 lbs.), consisting mostly of soluble carbohydrates and phenols not complexed to proteins, were kept for another application. The solids ejected by the centrifuge (218 lbs.) consisting of the phenol/protein complex, were collected and fed into an atomizing spray drier of standard design using a Moyno pump at 1 gallon per minute flow rate. The product was sprayed from an atomizer with 4 mm orifices into a 7 foot-high tower. The spray-drier inlet temperature was 410° F. and the outlet temperature was 190° F. 16 lbs. of product was obtained from the spray drier. The resultant product consisted of 63.9% protein, 4.1% moisture, 10.0% fat, 2.6% ash, and 19.4% carbohydrate. The product had an antioxidant capacity of 834 micromoles trolox equivalents per milligram.

Example 3

Introduction of Exogenous Phenols to a Hops Phenol/Protein Isolation 100 lbs. of defatted hops (*humulus lupulus* L.) flour and 1 lb. of quercetin were added to 100 gallons of water. pH was adjusted to 10.05 by adding 30% KOH. Temperature was held at 55° C. under constant agitation for 45 minutes. The resultant mixture was pumped into the same solids-ejecting disc centrifuge as described in Example 1. The solids ejected by the centrifuge, consisting mostly of wet plant hulls, fiber and other insolubles, were discarded. The liquids were pumped through a 20 micron cartridge prefilter into a second tank. pH was adjusted to 4.48 using 30% HCl to precipitate the phenol-protein complex. Temperature was kept at 55° C. for 30 minutes. The resultant mixture was pumped into a solids-ejecting disc centrifuge. The liquids that passed through the centrifuge (528 lbs.) consisting of soluble carbohydrates, soluble proteins, and soluble phenols not bound to insoluble protein, were retained for another application. The solids ejected by the centrifuge.(139 lbs.) consisting of the phenol/protein complex, were collected and fed into an atomizing spray drier of standard design using a Moyno pump at 1 gallon per minute flow rate. The product was sprayed from an atomizer with 4 mm orifices into a 7 foot-high tower. The spray-drier inlet temperature was 410° F. and the outlet temperature was 190° F.

11 lbs. of product was obtained from the spray drier. The resultant product consisted of 71.2% protein, 3.9% moisture, 8.8% fat, 3.0% ash, and 13.1% carbohydrate. The product had an antioxidant capacity of 590 micromoles trolox equivalents per milligram.

Example 4

Shake 3 lbs. of the phenolated buckwheat protein of Example 2 was mixed with 6 lbs. of soy protein isolate, 13 lbs. of crystalline fructose, 5 lbs. of Dutch processed cocoa, 0.2 lbs. stevia extract, 0.1 lbs. lecithin, 0.05 lbs. medium chain triglycerides, 0.09 lbs. ascorbic acid, 0.03 lbs. vitamin B acetate, 0.02 lbs. digestive enzyme mix (AMINOGEN™).

This made 150 30 gram packets. The packets were mixed with 8 oz. of skim milk to make a protein shake for use as a snack, exercise supplement, or meal replacement.

Example 5

Bar

The following Table provides the ingredients for an exemplary bar incorporating the phenolated protein of Example 3.

| Number | Ingredient | Weight % |
|---|---|---|
| 1 | Maltitol Syrup | 6.410 |
| 2 | Cocoa Powder | 4.487 |
| 3 | Chocolate Chips | 3.846 |
| 4 | Glycerine | 15.385 |
| 5 | Natural Flavors | 1.923 |
| 6 | Potassium Sorbate | 0.256 |
| 7 | Dicalcium Phosphate | 0.962 |
| 8 | Magnesium Oxide | 0.064 |
| 9 | Vitamin A Palmitate | 0.060 |
| 10 | Ascorbic Acid | 0.045 |
| 11 | Vitamin E Acetate | 0.015 |
| 12 | Niacinamide | 0.010 |
| 13 | Ferrous Fumarate | 0.010 |
| 14 | Zinc Oxide | 0.010 |
| 15 | Pantothenic Acid | 0.005 |
| 16 | Pyridoxine HCl | 0.001 |
| 17 | Copper Gluconate | 0.001 |
| 18 | Cholecalciferol | 0.0007 |
| 19 | Riboflavin | 0.0007 |
| 20 | ThiamineMononitrate | 0.0007 |
| 21 | Folic Acid | 0.0001 |
| 22 | Biotin | 0.00005 |
| 23 | Potassium Iodide | 0.0001 |
| 24 | Cyanocobalamin | 0.00001 |
| 25 | Soy Protein Isolate | 28.205 |
| 26 | Phenolated Hops Protein | 12.821 |
| 27 | Maltitol Syrup | 12.821 |
| 28 | Fractionated Vegetable Oils | 5.128 |
| 29 | Cocoa | 3.846 |
| 30 | Calcium Caseinate | 2.564 |
| 31 | Lecithin | 0.641 |
| 32 | Vanilla | 0.513 |
| 33 | Sucralose | 0.128 |

The composition was prepared by combining items 1, 2, and 3 from the above Table, and heating to 245° F., followed by transfer to a mixer. To the heated composition were added items 4, 5 and 6 of the Table and the mixture was agitated for over 2 minutes. The mixture was cooled to 140° F. and item 6 was added and mixed for 1 minute. To the mixture was then added a pre-blend of items 7-24 of the Table, followed by mixing for 2 minutes. Items 25 and 26 were then added and the resulting mixture agitated for 2 minutes. The mixture was allowed to cool and cut into rectangles or bars with each bar weighing approximately 60 grams. To each bar was added a coating consisting of a hot mixture (140° F.) of items 27 to 33 of the Table. Finally items 17-21 of the Table were added and the mixture agitated for 4 minutes. The resultant bars weighed approximately 80 grams and each contained approximately 10 grams of the phenolated hops protein of Example 3.

Example 6

Capsule 3 lbs. of the phenolated buckwheat protein of Example 2 was placed into size "0" hard-shell gelatin capsules in a capsule filling machine. 400 mg of phenolated buckwheat protein was filled into each capsule. 3400 capsules were obtained.

Example 7

Tablet 3 lbs. of the phenolated buckwheat protein of Example 2 was mixed with 1 lb. of calcium diphosphate and 0.1 lb. of magnesium stearate and placed in a Glatt fluid-bed granulator. The resultant agglomerated powder was introduced to a tablet press. 525 mg of the mixture was pressed into each tablet, representing 400 mg of phenolated buckwheat protein. 3100 tablets were obtained.

What is claimed is:

1. A process for preparing a dietary supplement comprising a pharmaceutically acceptable excipient, and vegetable protein bound phenolics, comprising the steps of:
   adding alkali to an admixture of vegetable flour with water where said flour comprises naturally occurring protein and naturally occurring phenolics until said aqueous admixture is of alkaline pH;
   allowing the naturally occurring phenolics to oxidize and covalently attach to the protein;
   removing solids from said admixture of alkaline pH;
   adding acid to the admixture until said admixture is of neutral or acidic pH thereby causing vegetable protein bound phenolics to precipitate as a solid;
   isolating the solid precipitate, and
   admixing the vegetable protein bound phenolics constituting a solid precipitate with a pharmaceutically acceptable excipient.

2. A process in accordance with claim 1 wherein the vegetable flour is from a source selected from a group consisting of buckwheat, sunflower seeds, soy beans, hops, mustard seeds, cottonseeds, peanuts, safflower seeds, rape seed and flax seeds.

3. A process in accordance with claim 1 additionally comprising the step of drying the solid precipitate before the step of admixing it with a pharmaceutically acceptable excipient.

4. A process in accordance with claim 1 wherein the dietary supplement comprises approximately 25 to 95 percent by weight of the vegetable protein bound phenolics.

5. A process in accordance with claim 1 additionally comprising the step of making unit doses of said dietary supplement wherein each unit dose of the supplement has an antioxidant capacity of 2,500 to 200,000 micromoles of trolox equivalent per unit dose of the supplement.

6. A process in accordance with claim 1 additionally comprising the step of adding exogenous phenolics to the admixture of vegetable flour with water.

7. A process in accordance with claim 6 wherein exogenous phenolics are added to the admixture in a ratio of approximately 0.25 to 5 weight units of exogenous phenolics to 100 weight units of vegetable flour.

8. A process in accordance with claim 7 wherein exogenous phenolics are added to the admixture in a ratio of approximately 0.5 to 2.0 weight units of exogenous phenolics to 100 weight units of vegetable flour.

9. A process for preparing a food product comprising a pharmaceutically acceptable excipient, and vegetable protein bound phenolics, wherein said food product has an antioxidant capacity of 50 to 2,000 micromoles of trolox equivalent per gram of the food product, the process comprising the steps of:

adding alkali to an admixture of vegetable flour with water where said flour comprises naturally occurring protein and naturally occurring phenolics until said aqueous admixture is of alkaline pH;

allowing the naturally occurring phenolics to oxidize and covalently attach to the protein;

removing solids from said admixture of alkaline pH;

adding acid to the admixture until said admixture is of neutral or acidic pH thereby causing vegetable protein bound phenolics to precipitate as a solid;

isolating the solid precipitate, and admixing the vegetable protein bound phenolics constituting a solid precipitate with a nutritional product.

10. A process in accordance with claim 9 additionally comprising the step of drying the solid precipitate before the step of admixing it with a nutritional product.

11. A process accordance with claim 9 wherein the food product is in the form of edible bars or liquid shakes.

12. A process in accordance with claim 9 additionally comprising the step of adding exogenous phenolics to the admixture of vegetable flour with water.

13. A process in accordance with claim 9 wherein exogenous phenolics are added to the admixture in a ratio of approximately 0.25 to 5.0 weight units of exogenous phenolics to 100 weight units of vegetable flour.

14. A process in accordance with claim 9 wherein exogenous phenolics are selected from a group consisting of phenolic acids, catechins, flavones, anthocyanidins and isoflavones.

* * * * *

UNITED STATES PATENT AND TRADEMARK OFFICE
CERTIFICATE OF CORRECTION

PATENT NO. : 7,226,626 B2  Page 1 of 1
APPLICATION NO. : 10/834333
DATED : June 5, 2007
INVENTOR(S) : Yatcilla It is certified that error appears in the above-identified patent and that said Letters Patent is hereby corrected as shown below:

Column 2, line 32, "flee" should be -- free --.

Column 9, line 13, "vitamin B" should be -- vitamin E --.

Signed and Sealed this

Eleventh Day of December, 2007

JON W. DUDAS
*Director of the United States Patent and Trademark Office*